US00PP17944P3

(12) United States Plant Patent
Brand

(10) Patent No.: US PP17,944 P3
(45) Date of Patent: Aug. 28, 2007

(54) ***PANICUM* PLANT NAMED 'RR1'**

(50) Latin Name: *Panicum virgatum*
Varietal Denomination: RR1

(75) Inventor: Mark H. Brand, Willington, CT (US)

(73) Assignee: University of Connecticut, Farmington, CT (US)

( * ) Notice: Subject to any disclaimer, the term of this patent is extended or adjusted under 35 U.S.C. 154(b) by 430 days.

(21) Appl. No.: 11/096,302

(22) Filed: Apr. 1, 2005

(65) Prior Publication Data

US 2006/0225179 P1 Oct. 5, 2006

(51) Int. Cl.
*A01H 5/00* (2006.01)

(52) U.S. Cl. ..... Plt./384

(58) Field of Classification Search ..... Plt./384
See application file for complete search history.

(56) References Cited

U.S. PATENT DOCUMENTS

| | | | |
|---|---|---|---|
| PP11,202 | P | 2/2000 | Smith et al. |
| PP12,505 | P2 | 4/2002 | Slaughter et al. |
| PP14,305 | P2 | 11/2003 | Moonen |
| PP15,450 | P2 | 12/2004 | Vandenberg |
| 2005/0066399 | P1 | 3/2005 | Tate |

*Primary Examiner*—Kent Bell
*Assistant Examiner*—Annette H Para
(74) *Attorney, Agent, or Firm*—Edwards Angell Palmer & Dodge LLP

(57) ABSTRACT

A distinct cultivar of *Panicum* plant named 'RR1', characterized by a base blue-green foliage developing into predominately dark purple-red foliage color by early to mid-summer, easy propagation, vigorous growth and compact growth habit. The unique purple-red color developing at mid-season enhances commercial value as an ornamental.

3 Drawing Sheets

Botanical classification: *Panicum virgatum* cultivar 'RR1'.

BACKGROUND OF THE INVENTION

The present invention relates to a new and distinct cultivar of *Panicum* plant, botanically known as *Panicum virgatum* and hereinafter referred to by the name 'RR1'.

The new *Panicum* is a variety of switchgrass and was the result of a controlled cross between the female, or seed, parent *Panicum virgatum* 'Heavy Metal' (unpatented) and the male, or pollen, parent *Panicum virgatum* 'Haense Herms' (unpatented). The new cultivar was discovered and selected by the Inventor as the best individual among 300 seedlings in Storrs, Conn. in 2002. The selection of this plant was based on its color and vigorous growth habit.

Asexual reproduction of the new cultivar by divisions taken over time since August, 2003 in Storrs, Conn., has shown that the unique features of this new *Panicum* are stable and reproduced true to type in successive generations.

SUMMARY OF THE INVENTION

The cultivar 'RR1' has not been observed under all possible environmental conditions. The phenotype may vary somewhat with variations in environment such as temperature, soil type, daylength, water/fertilization frequency and light intensity; however, without any variance in genotype.

The following traits have been repeatedly observed and are determined to be the unique characteristics of 'RR1'. These characteristics in combination distinguish 'RR1' as a new and distinct cultivar of *Panicum*.

1. Base foliage is blue-green with purple-red color developing on most leaves by midsummer (July in Connecticut).
2. Over two-thirds of the leaf area of the foliage develops a rich purple-red to burgundy color by midsummer (July).
3. Easily propagated.
4. Vigorous growth characteristics.
5. Compact growth habit.

Similar to other switch grasses, the new cultivar is tolerant of a wide range of soil and climatic conditions and is easily cultivated in sunny landscapes. It has an erect, upright form, showy flowers, yellow fall color and interesting winter silhouette. The new plant is most distinguished from other switch grasses known to the inventor both by its base foliage color which differs from typical switch grasses that have dark green to gray-green foliage and by the distinct rich red foliage color that develops mid-season.

Plants of the new *Panicum* can be compared to plants of the seed parent, 'Heavy Metal'. In side-by-side comparisons made in Storrs, Conn., both plants exhibited blue-green foliage; however, in contrast to 'RR1', 'Heavy Metal' does not develop red foliage.

In comparison with its pollen parent, 'Haense Herms', 'RR1' differs in having blue-green base foliage while the pollen parent has a base foliage color of green. The pollen parent 'Haense Herms' develops significant red foliage in late summer to early fall in contrast to 'RR1' which develops purple-red foliage by midsummer.

The switch grass 'Dallas Blues' (U.S. Plant Pat. No. 11,202) is similar to 'Heavy Metal' in that is possesses blue-green foliage and does not develop red foliage, thus distinguishing it from 'RR1'. Moreover, 'Dallas Blues' is 3–4 times taller than 'RR1'.

The cultivar 'Rotstrahlbusch' has red-tipped foliage but significant red color does not develop until late summer to fall; moreover, the base foliage color, like 'Haense Herms' is green, not blue-green.

These comparisons are shown in Table 1.

TABLE 1

| | Base Foliage Color | Color Development (Purple-Red) | Height (cm) |
|---|---|---|---|
| 'RR1' | Blue-green | Mid-season (July) | 55 |
| 'Heavy Metal' | Blue-green | None | 135 |
| 'Haense Herms' | Green | Late season (August-September) | 100 |
| 'Dallas Blues' | Blue-green | None | 193 |
| 'Rotstrahlbusch' | Green | Late season (August-September) | 110 |

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description, which do accurately describe the colors of the new plant. All photographs were taken on plants grown in Storrs, Conn. at the University of Connecticut Research Farm.

The photograph on the first sheet shows a single plant growing in the field in full sun in mid-July.

The photograph in the second sheet is a closeup view of typical red foliage color development by mid-July.

The photograph in the third sheet comprises plants in a trial row in mid-July.

DETAILED BOTANICAL DESCRIPTION

In the following description, color references are made to The Royal Horticultural Society Colour Chart (R.H.S.), 1986 Edition, except where general terms of ordinary dictionary significance are used. The R.H.S. colors were related to chromameter measurements made under natural daylight conditions.

Measurements made with a Minolta Chromameter CR-200 were converted to R.H.S. color references. The minolta measures color on three axes against white to black, green to red, and blue to yellow to obtain numbers that are converted by equations to L, H, and C. L represents the measured color relative to black (dark) to white (light) on a scale of 0–100. H represents a hue angle based on 360 where degrees in an arc area around 360 represent color ranges; e.g., the red-purple range at 315° is a purple color while 30° appears red. C, or chroma, is a measure of color saturation based on a scale of 0–60. A high chroma number represents a more intense color.

The following observations and measurements describe plants grown in Storrs, Conn. under full sun outdoor conditions. Average daytime temperatures in Connecticut during April–October are 55°–78° F. Average nighttime temperatures during these months average 33°–59° F.

Botanical classification: *Panicum virgatum* cultivar 'RR1'.

Parentage:

*Female or seed parent.*—*Panicum virgatum* 'Heavy Metal'.

*Male or pollen parent.*—*Panicum virgatum* 'Haense Herms'.

Propagation:

*Type.*—By divisions.

Plant description:

General appearance: Herbaceous perennial grass with an upright, vase-shaped habit with overarching leaf blades. Grass clumps are dense and multistemmed. Overall the foliage appears blue-green in the spring and then develops strong dark red color over two thirds or more of the leaf area by early to mid summer. Airy flower clusters develop at the top of the plant at the terminal of most culms. Flower/seed clusters persist from late summer into early winter.

Root description: wiry, fibrous.

Rhizomes: Slightly creeping.

Mature plant:

*Height.*—55 cm.

*Width.*—60–70 cm.

Foliage:

*Arrangement.*—Alternate, erect, sheathed.

*Shape.*—Linear.

*Margin.*—Entire.

*Aspect.*—Flat.

*Length.*—35–40 cm.

*Width.*—1 cm.

*Texture.*—Upper and lower surfaces smooth and glaucous.

*Color.*—Base foliage: green merging to blue: green: RHS 137D (L=56; hue angle=136; chroma=30); blue: RHS 133B (L=53; hue angle=171; chroma=19).

*Purple-red foliage portions.*—Red: RHS 59A, 185A, 184A (L=36, hue angle=11, chroma=36); dark purple: RHS 79A (L=34, hue angle=315, chroma=11).

Flower description:

*Inflorescence.*—Panicles fine textured, spreading and feathery.

*Flowering.*—Begins in early to mid-August with flower clusters typically numerous by early September in Northern Hemisphere.

*Panicle length.*—20–27 cm.

*Panicle width.*—17–20 cm.

Seed production: Limited amount depending on size of seed head, comparable to other switch grasses.

Disease resistance: Comparable to other members of this species.

Pests: No insect problems have been observed in the parent or progeny, as is typically observed for this species.

It is claimed:

1. A new and distinct cultivar of *Panicum* plant as illustrated and described.

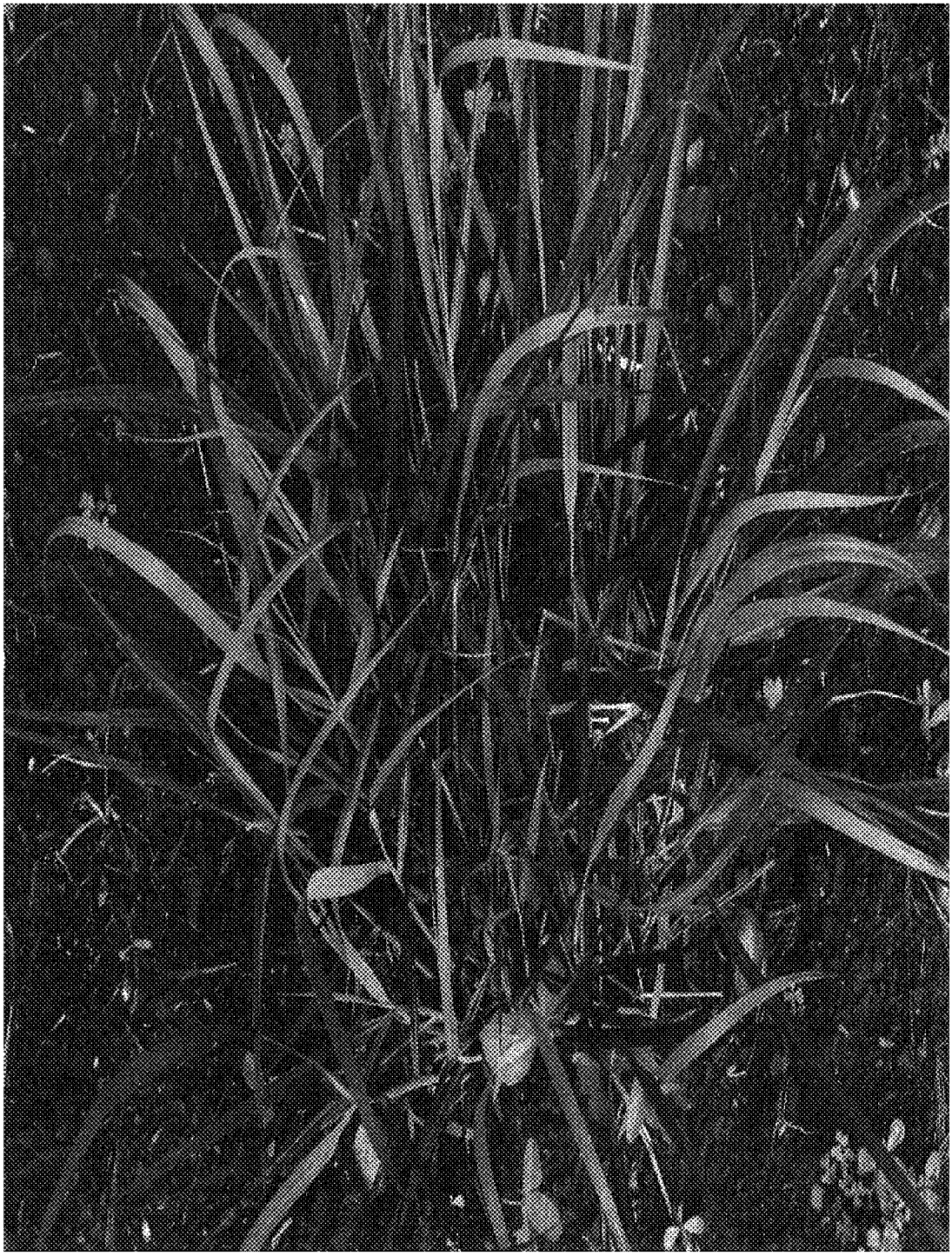

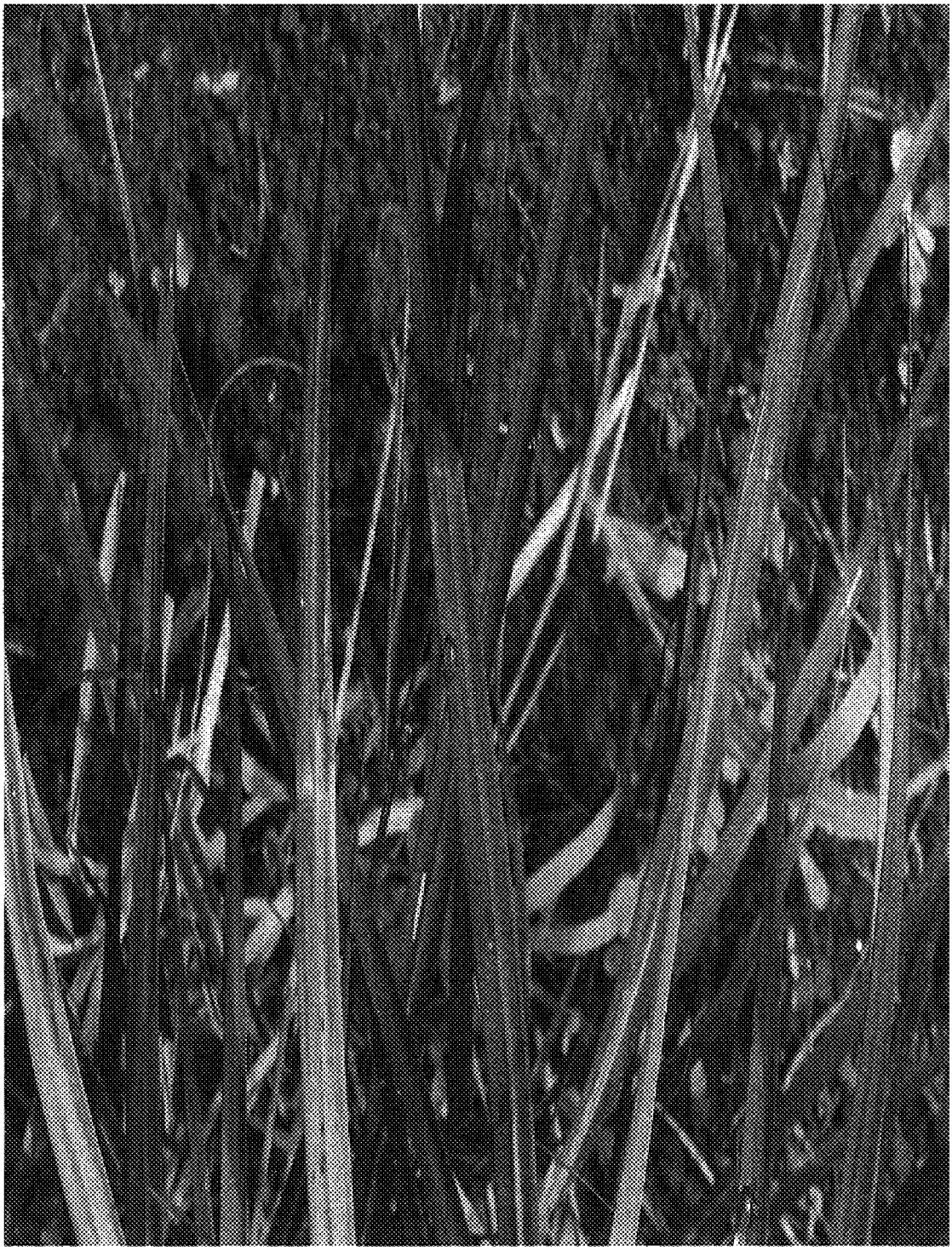

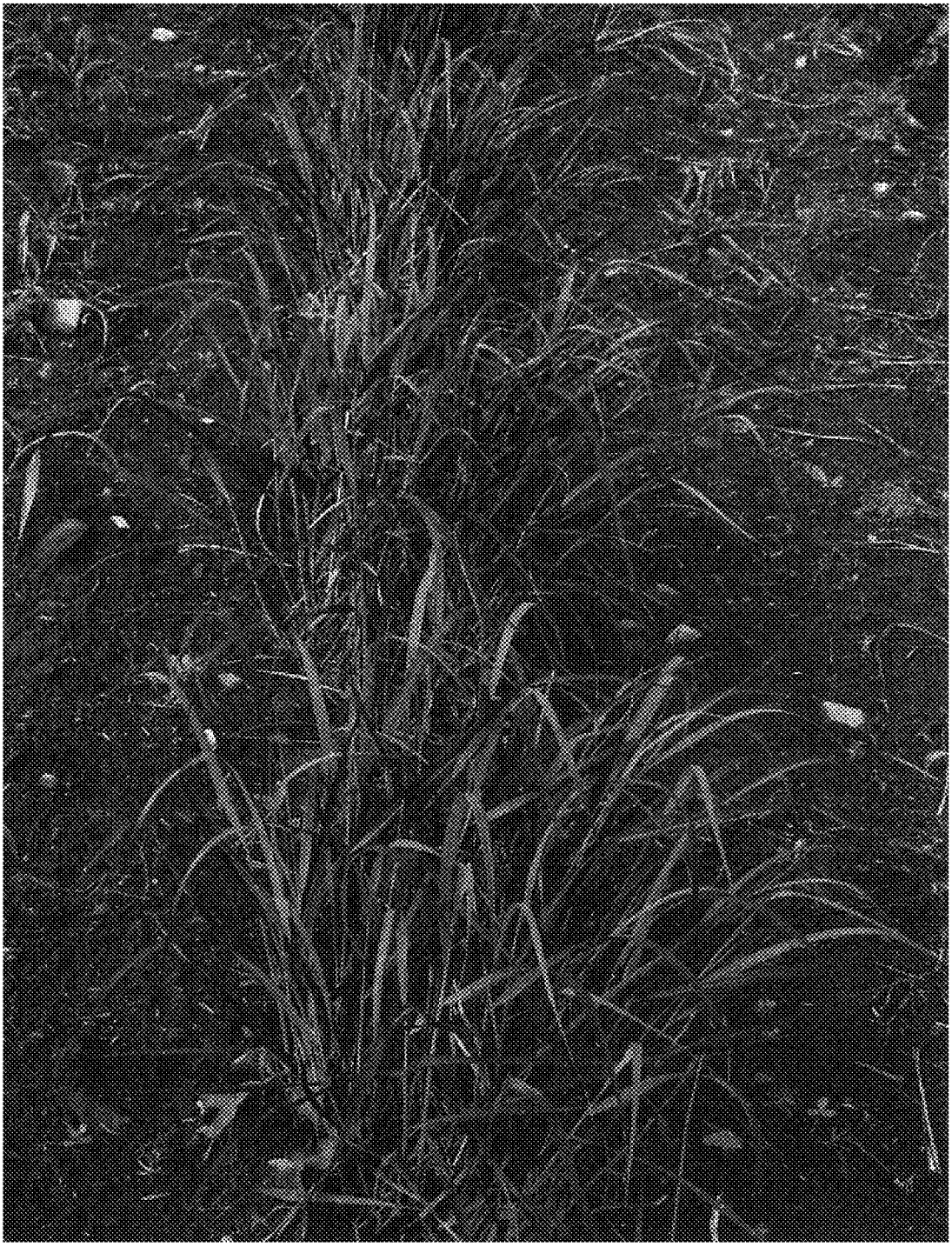

* * * * *